(12) United States Patent
Yu

(10) Patent No.: US 10,912,324 B2
(45) Date of Patent: Feb. 9, 2021

(54) FOOD PRODUCT FOR IMPROVING LYMPHATIC CIRCULATION

(71) Applicant: Heong Jun Yu, Incheon (KR)

(72) Inventor: Heong Jun Yu, Incheon (KR)

(*) Notice: Subject to any disclaimer, the term of this patent is extended or adjusted under 35 U.S.C. 154(b) by 0 days.

(21) Appl. No.: 15/959,265

(22) Filed: Apr. 22, 2018

(65) Prior Publication Data

US 2019/0110511 A1 Apr. 18, 2019

(30) Foreign Application Priority Data

Oct. 15, 2017 (KR) ........................ 10-2017-0133688

(51) Int. Cl.
| | | |
|---|---|---|
| *A61K 36/752* | (2006.01) | |
| *A61K 36/00* | (2006.01) | |
| *A23L 33/105* | (2016.01) | |
| *A61K 36/234* | (2006.01) | |
| *A61K 36/8994* | (2006.01) | |
| *A61K 36/25* | (2006.01) | |
| *A23L 33/125* | (2016.01) | |

(52) U.S. Cl.
CPC ........... *A23L 33/105* (2016.08); *A23L 33/125* (2016.08); *A61K 36/234* (2013.01); *A61K 36/25* (2013.01); *A61K 36/752* (2013.01); *A61K 36/8994* (2013.01); *A23V 2002/00* (2013.01); *A23V 2200/326* (2013.01); *A23V 2250/21* (2013.01)

(58) Field of Classification Search
None
See application file for complete search history.

(56) References Cited

FOREIGN PATENT DOCUMENTS

| | | | |
|---|---|---|---|
| CN | 1274599 A | * | 11/2000 |
| CN | 103127433 A | * | 6/2013 |
| CN | 106668704 A | * | 5/2017 |
| JP | 2016135781 A | * | 7/2016 |
| KR | 2011138459 A | * | 12/2011 |
| KR | 1768806 B1 | * | 8/2017 |

* cited by examiner

*Primary Examiner* — Michael Barker
*Assistant Examiner* — Randall O Winston
(74) *Attorney, Agent, or Firm* — Ryuh Patent Law; Steven Yu

(57) ABSTRACT

Disclosed is a food composition which promotes lymphatic circulation in the body to improve the environment around the cells and to help normal metabolism of the cells. The food composition according to the present invention includes cnidium, maple syrup, dried bigarade orange, bambusae succus, kalopanax and coix in the form of powder, liquid or extract.

2 Claims, 2 Drawing Sheets

FOOD PRODUCT FOR IMPROVING LYMPHATIC CIRCULATION

BACKGROUND

The present invention relates to a food composition, and more particularly, to a food composition capable of promoting lymphatic circulation to improve the environment around a cell and restore normal metabolism of cells.

The inventor of the present invention has learned from many clinical experiences that smooth lymphatic circulation plays an important role in maintaining a healthy body state and in rapidly recovering a diseased body.

Body fluid circulation involves both blood circulation and lymphatic circulation and is responsible for physical circulation of the body. The blood circulation plays a pivotal role in the material circulation of the body, and the lymphatic circulation plays an auxiliary role in helping the material circulation of the cardiovascular system.

The lymphatic system consists of lymphatic fluid, lymphatic vessels, and lymph nodes. They are responsible for returning body fluids that may be excessively present between the tissues of the human body to the heart. It also plays a role in transferring the remaining waste after cell metabolism and cell metabolite such as fat or protein with high molecular weight that does not pass through capillary tube from tissue to blood through the vena cava.

The lymphatic capillaries are located adjacent to the blood capillaries and distributed throughout the body. The tissue fluid in the tissue enters the lymphatic capillaries and becomes lymph fluid. When the tissue fluid enters the lymphatic system, it does not pass through the membrane, unlike the blood capillaries, but through the small holes at the end of the lymphatic capillaries. Therefore, materials with high molecular weight that cannot pass through the membrane of the capillary blood vessels can easily pass through, and most of the components of the tissue fluid are contained in the lymph fluid. The end portion of the lymphatic capillary has a structure that is difficult for lymphatic fluid to escape from the lymphatic capillary.

The composition of the lymph fluid is similar to that of the tissue fluid, and consists of water, dead cells, fat and protein, salt, sugar, urea, and lymphocytes. The lymphatic vessel is the passage through which the lymph fluid is transported from the tissue to the large vena cava. The lymphatic canal is divided into a superficial lymphatic vessel between the skin and the fascia and a deep lymphatic vessel located below the fascia.

Therefore, a superficial lymphatic vessel plays an important role in the lymphatic circulation, and it is possible to promote the lymphatic circulation through the lymphatic massage stimulating the skin physically. The movement of the lymphatic fluid is mainly caused by the small motive force associated with the contraction and relaxation of the muscles and the valves in the lymphatic vessels. When the muscle is contracted, the thickened part of the muscle pushes the lymphatic vessel and reduces the volume inside the lymphatic vessel. At this time, the lymphatic fluid moves in the direction of the heart by the volume of the reduced lymphatic vessel, not in the direction blocked by the valve. On the other hand, when the muscle relaxes, it becomes partially tapered and the volume of the inside of the lymph vessel increases as the pressed lymphatic vessel recovers. At this time, the lymph fluid should be replenished by an increased volume, but it cannot come from the cardiac direction clogged with the valve, and it comes from the direction far from the heart. Thus, one section of the valve acts as a small heart-like pump that helps the lymphatic circulation along with the movement of the muscles. In addition, since these small pumps are connected in series, muscle movements in long sections such as the arms and legs act as a power source for strongly promoting the movement of the lymphatic fluid.

The capillary lymph vessels, which are closer to the skin than the blood capillaries, are susceptible to pathogenic microorganisms such as bacteria and viruses even for minor damage to the skin. To compensate for this, lymph nodes are present before the lymphatic vessels reach the vena cava. The lymph nodes are net-shaped and can be clogged with internal net structures, so they are mainly distributed in the ear, under the tongue, underarms, groin, etc., where large muscles exist or large muscle movements occur. Lymph nodes produce lymphocytes to protect the body against invasion by pathogens and function to break down and eliminate pathogens such as bacteria and viruses in the lymph fluid and dead cells and waste products before returning to the blood. The migration of the lymph fluid begins when the tissue fluid enters the lymphatic capillary. The lymphatic capillaries join the lymphatic vessels, and the lymphatic vessels have lymphatic valves that prevent the lymphatic fluid from regurgitation and make the circulatory power of the lymphatic fluid like a vein valve. The lymph fluid passes through the lymph nodes, which act as a barrier to microbial invasion, and joins with blood in the large vena cava. Therefore, the lymphatic circulation starts from the fingertips, toes and head ends and proceeds toward the heart. After passing through the lymph nodes in the armpits, groin, under the ear and under the tongue, the pathogenic microorganisms and waste products in lymphatic fluid are filtered out.

Thus, the lymphatic system is an auxiliary circulatory system that is closely related to cardiovascular and helps the body fluid circulation. When the material is exchanged between the capillaries and the tissue, the amount of fluid that flows structurally from the capillary to the tissue is always greater than the amount that enters the capillary in the tissue. At this time, when the remaining fluid accumulates, edema occurs in the tissue and hydrostatic pressure increases. The blood also becomes dry and sticky due to the lack of fluids. If these phenomena continue unimproved, they cause serious problems of fluid circulation and cause many problems. The lymphatic system plays a role in improving such an imbalance by allowing the body fluids accumulated in the tissue to move to the large vena cava through the lymphatic duct, a pathway through which body fluids can move from the tissue to the vena cava. Therefore, in the human body, edema means a disorder of body fluid circulation, and body fluid circulation disorder means a lymphatic circulation disorder. In addition, improvement of the edema of the human body means improvement of body fluid circulation disorder, whether improvement of systemic edema or local edema, and improvement of body fluid circulation disorder means improvement of lymphatic circulation disorder.

Lymphatic circulation is a process of gathering stagnant fluid inside the body and returning it to the blood through the umbilical vein. In the process, it promotes the release of waste products and makes it possible to recycle what is needed. From the viewpoint of merely fluid circulation, blood circulation is more important than lymphatic circulation. However, from the viewpoint of tissue environment affecting cell metabolism, lymph circulation directly involved in circulation of tissue fluid is more important than blood circulation. The lymphatic circulation firstly promotes the blood circulation of the cardiovascular system and promotes the supply of nutrients, water, oxygen and hormones, which are necessary for the cells, and at the same time, quickly removes the waste materials, toxic substances, inflammation substances, helping to create an optimal environment for cells to function normally. It also helps absorption and movement of ingested medicines and nutrients, and delivers them quickly to the site of need to increase effectiveness. Thus, lymphatic circulation plays an important role in promoting optimal conditions for cell activation, and is thus an important factor for the human body to function in a healthy manner.

Lymphatic circulation disorder causes systemic edema or local edema because the body fluid accumulated in the tissue remains in the tissue without returning to the blood through the lymphatic circulation. That is, systemic edema or local edema of the body can all be considered as a disturbed lymphatic circulation. This edema is not a big problem in a short period of time, but if it lasts for a long time, it will lower the metabolic function of the site and cause many diseases. Considering that muscle movement is the only power of the lymphatic circulation, all the symptoms that can be caused by lack of exercise are symptoms of lymphatic circulation disorder, and all the effects that can be improved by exercise can be obtained by promoting the lymphatic circulation. The lymphatic circulation gains circulatory power only by the muscle movement, and the modern man who does not need the movement for survival lacks the opportunity of the muscular exercise, and the lymph circulation is not achieved smoothly.

Therefore, it is an urgent task to find a way to promote lymphatic circulation in modern people who lack body fluency due to lack of exercise. Nonetheless, there have been many discussions and countermeasures on blood circulation, but there is a lack of discussion about the importance of lymphatic circulation. The concept of lymphatic circulation has not yet been recognized as medically important compared with realistic importance, and the development of medicines is also in short supply.

SUMMARY

An object of the present invention is to provide a food composition capable of promoting the lymphatic circulation in the body, improving the environment around the cells and helping normal metabolism of the cells.

Another object of the present invention is to provide a food composition capable of ameliorating various symptoms that may be caused by a lymphatic circulation disorder.

Embodiments of the present invention provide a food composition comprising cnidium, maple syrup, dried bigarade orange, bambusae succus, kalopanax and coix in the form of powder, liquid or extract.

In some embodiments, the food composition can be made into pill, granules, or powders by mixing maple syrup and bambusae succus in a mixed powder of cnidium, dried bigarade orange, kalopanax and coix.

In other embodiments, the food composition can be made into pill, granules, powders or liquid by mixing maple syrup and bambusae succus into an extract extracted from a mixture of cnidium, dried bigarade orange, kalopanax and coix.

In still other embodiments, the food composition can be made into pill, granules, powders or liquid containing the extract extracted from a mixture of cnidium, maple syrup, dried bigarade orange, bambusae succus, kalopanax and coix as an active ingredient.

BRIEF DESCRIPTION OF THE DRAWINGS

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION OF THE EMBODIMENTS

Figure 1:
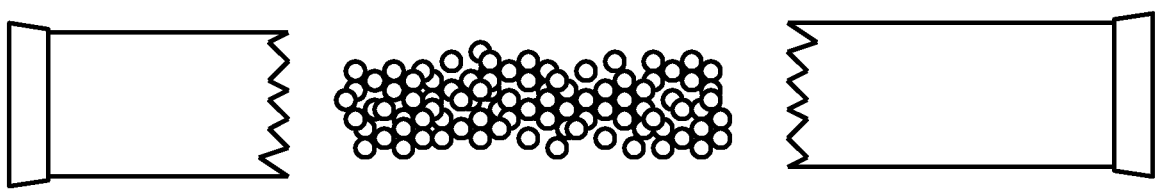
FIG. 1 is a photograph of the contents of a product of a food composition according to the present invention.
Figure 1:
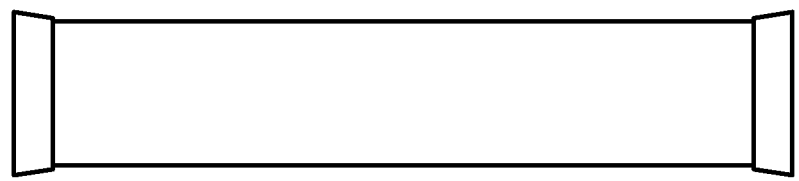
Figure 1:
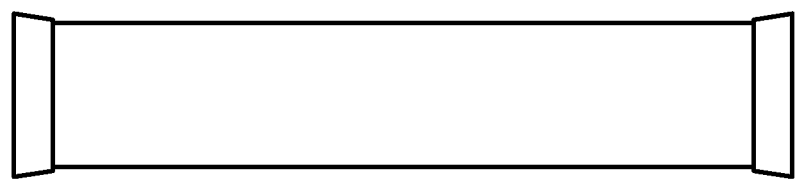

Hereinafter, exemplary embodiments will be described in more detail with reference to the accompanying drawings.

The food composition according to the present invention comprises, cnidium, maple syrup, dried bigarade orange, bambusae succus, kalopanax and coix in powder, liquid or extract form.

The food composition according to the present invention is composed of the following composition components and composition ratios.

i) 20 to 50% by weight (based on total weight, the same applies hereinafter) of cnidium;
ii) 20 to 50% by weight of maple syrup;
iii) 10-30% by weight of dried bigarade orange;
iv) 10-30% by weight of bambusae succus;
v) 5-25% by weight of kalopanax; and
vi) 1 to 20% by weight of coix.

When cnidium is added in an amount of less than 20% by weight, the effect of promoting lymphatic circulation by cnidium is insignificant. If cnidium is added by more than 50% by weight, the effect of promoting lymphatic circulation by cnidium is not increased.

When maple syrup is added at less than 20% by weight, the effect of promoting lymphatic circulation by maple syrup is insignificant. If maple syrup is added by more than 50% by weight, the effect of maple syrup on lymphocyte promotion is not increased.

When dried bigarade orange is added at less than 10% by weight, the effect of promoting lymphatic circulation by dried bigarade orange is insignificant. If dried bigarade orange is added by more than 30% by weight, the effect of dried bigarade orange on lymphocyte promotion is not increased.

When bambusae succus is added at less than 10% by weight, the effect of promoting lymphatic circulation by bambusae succus is insignificant. If bambusae succus is added by more than 30% by weight, the effect of bambusae succus on lymphocyte promotion is not increased.

When calopanax is added at less than 5% by weight, the effect of promoting lymphocyte recirculation by calopanax is insignificant. If kalopanax is added by more than 25% by weight, the effect of calopanax on the promotion of lymphocyte circulation is not increased.

When coix is added in an amount of less than 1% by weight, the effect of promoting lymphatic circulation by coix is insignificant. If coix is added in an amount exceeding 20% by weight, the effect of promoting lymphocyte circulation by coix is not increased.

The food composition according to the present invention can be made into pill, granules, or powders by mixing maple syrup and bambusae succus into a mixed powder of cnidium, dried bigarade orange, kalopanax and coix.

The food composition according to the present invention can be made into pill, granules, powders or liquid by mixing maple syrup and bambusae succus into an extract extracted from a mixture of cnidium, dried bigarade orange, kalopanax and coix. To obtain the extract from the mixture, water or ethanol, or water and ethanol may be used. The extract may be a liquid or a dried powder.

The food composition according to the present invention can be made into pill, granules, powders or liquid containing an extract extracted from a mixture of cnidium, maple syrup, dried bigarade orange, bambusae succus, kalopanax and coix as an active ingredient. To obtain the extract from the mixture, water or ethanol, or water and ethanol may be used. The extract may be a liquid or a dried powder.

Cnidium is dried in the rootstock of the falciparum or the falciparum plant, and the taste is spicy and the quality is warm. Cnidium is known to contain cnidium-lactone, cedaric acid, and terpene alcohols.

Maple syrup is a concentrated and collected sap of Canadian maple and is widely used as a substitute for sugar.

Dried bigarade orange is mature fruit of citrus tree and is known to improve digestion defects.

Bambusae succus is a collection of sap of bamboo that is evaporated by strong heat in the process of making charcoal with bamboo.

Kalopanax is a dried Kalopanax pictus Nakai bark.

Coix is a seed of adlay millet. Adlay millet is planted in various parts of Korea. In the fall, the seeds are ripe, and then the topping is cut and dried, and the seeds are peeled off.

Among them, bambusae succus, kalopanax and maple syrup have the most direct and powerful effect on promoting lymphocyte irrespective of the ratio of their components. Therefore, if any one of bambusae succus, kalopanax and maple syrup is omitted, the lymphocyte stimulatory effect is markedly reduced. Cnidium, dried bigarade orange, and coix supplement and enhance the lymphocyte stimulating effect of bambusae succus, kalopanax and maple syrup. The food composition according to the present invention exhibits various effects such as improvement of edema, improvement of inflammation and pain, elimination of bruises, control of body temperature, improvement of cell environment, promotion of drug delivery, etc., by adding cnidium, dried bigarade orange and coix.

The constituent materials of the present invention as described above are all registered as safe natural food ingredients in the Korea Food & Drug Administration.

Since the promotion of lymphatic circulation creates an optimal environment for the metabolism of cells, the food composition according to the present invention can be utilized for almost all symptoms caused by inappropriate cell metabolic environment. In a narrow range, not only can it be used for improving edema, improving pain, improving inflammation, controlling body temperature, eliminating bruises, promoting drug delivery, and broadening it to be useful for all symptoms that can be caused by lack of exercise. In addition, the food composition according to the present invention can be applied to almost all fields for disease prevention, symptom improvement, and disease treatment.

It does not cause problems even when it is mixed with drugs or functional foods having different functions, rather it also helps absorption and delivery of active ingredients and also improves the cellular environment of the symptom-causing part, thereby enhancing the efficacy of the active ingredient. For example, when the food composition according to the present invention is taken together with vitamin C, a lipid-soluble blood circulating agent, etc., the effect of surely raising these effects is obtained.

The food composition according to the present invention basically improves the environment around the cells by allowing the lymphatic circulation to be smoothly performed in the body, helps to restore the normal metabolism of the cells, and makes the environment so that cells in the body can be normally activated. Directly, it promotes lymphatic circulation in the body, improving edema, improving inflammation and pain, removing bruises, controlling body temperature, improving cell environment, and promoting drug delivery.

1) Effect of improving edema: The promotion of lymphatic circulation according to the present invention basically involves circulating body fluid accumulated in a tissue through a lymphatic tube so as to be combined with blood in the great vena cava, thereby allowing the body fluid to be included in the systemic circulation. The effect is the improvement of edema. Edema refers to the congestion of body fluids. The body fluid in the human body can be solved only by the lymphatic circulation. Since fluid circulation is achieved through lymphatic circulation, congestion of body fluids represents a disturbance of lymphatic circulation. The edema or swelling disappears when the congestion of body fluid is removed. Therefore, it can be directly confirmed that the lymphatic circulation is improved by the improvement of edema according to the present invention. The following effects are, of course, physiologically predictable effects when the lymphatic circulation is promoted.

2) Improvement of inflammation and pain: Muscle pain is mainly caused by excessive use of muscle. In muscle fibers, the sensory nerve is loosely wound like a coil. Therefore, when the muscle fiber is excessively contracted, edema occurs due to the accumulation of lactic acid, inflammatory substances, etc., and the muscle fiber becomes thicker than a certain degree, the sensory nerve is physically pulled tightly to show pain. Having such a structure is intended to prevent damage to muscles, ligaments, joints, and bones that are likely to occur due to excessive contraction or edema of the muscles. When there is a slight swelling of the muscle fiber, there is no pain when moving or lightly moving, but when the exercise is strong, the pain appears. In severe muscle fiber swelling, the sensory nerve fibers, which wrap around the muscle fibers, are stretched and painful, even if there is no muscle contraction. In both cases, when the edema of the muscle fiber is rapidly improved by the stimulation of the lymphatic circulation according to the present invention, the pain is reduced, and at the same time, the inflammatory substance causing the edema is also escaped and the inflammatory state is also improved. Tendon pain is also caused by excessive use of muscles. Sensory nerve fibers in the tendons are loosely attached like spider webs. Therefore, when the tendons swell due to the accumulation of lactic acid, inflammatory substances, or excessive stretching of the muscle fibers due to excessive contraction of the muscle fiber, the sensory nerve is pulled physically tightly to cause pain. This structure is intended to prevent damage to muscles, tendons, ligaments, joints, bones, etc., which are likely to occur due to excessive contraction of the muscles. When there is a slight swelling of the tendon, it does not show pain if it does not move or lightly move, but when it exercises hardly, it shows pain. If the tendon swelling is severe, the sensory nerve fibers, which are wrapped around the tendons, are pulled tight and painful even if they do not move. In both cases, when the edema of the tendon is improved by promoting the lymphatic circulation according to the present invention, the pain is reduced, and the inflammatory substance causing the edema is also reduced, thereby reducing the inflammation. The lymphatic circulation helps circulation of body fluids and improves pain in muscles and tendons.

3) Improvement of cell environment: Promotion of lymphatic circulation improves the surrounding environment of the body tissues and helps the normal metabolism of cells. The lymphatic circulation promotes the blood circulation of the cardiovascular system first, thereby promoting the supply of the nutrients, water, oxygen, and hormones necessary for the cells, and at the same time, rapidly removing the waste, toxic substances and inflammatory substances accumulated in the tissues or cells, to create an optimal environment for normal operation. This allows the cells to efficiently utilize the nutrients and oxygen in the body and has an immediate effect.

4) Bruise Removal Effect: The bruise is a lump formed by the blood outside the blood vessel and under the skin when the blood vessel is ruptured due to bruising or various causes, and it appears red or black due to the red blood cells in the blood. At this time, the erythrocytes contained in the bruise cannot pass through the blood capillary wall due to its high molecular weight, so it must be disintegrated in situ or removed by the lymphatic circulation. The promotion of lymphatic circulation according to the present invention promotes the movement of a substance having a large molecular weight which cannot pass through the capillary wall, thereby rapidly removing the bruise.

5) Body Temperature Regulating Effect: Promotion of lymph circulation according to the present invention improves circulation of body heat through circulation of body fluids. Lymph circulation promotes transmission and dispersion of body heat and improves cellular metabolism to normalize low body temperature locally. When body temperature is high, body temperature is lowered by normalizing body temperature.

6) Effect of Drug Delivery Promotion: Promotion of Drug Delivery Promotion: When a drug prescribed for a specific disease is administered or an injection is administered, when the lymphocyte is promoted by the present invention, the drug is rapidly and sufficiently transferred to the lesion. Therefore, the effect of the drug appears clearly in the lesion.

EXAMPLE

For the clinical test and confirmation of the effect of the food composition according to the present invention, the food composition pill for internal use was prepared several times in the following amounts.

First, a mixture of 2,700 g of cnidium powder, 1,400 g of dried bigarade orange powder, 1,100 g of kalopanax powder, 800 g of coix powder, 2,600 g of maple syrup and 1,400 g of bambusae succus was prepared. The mixture was formed into a pill having a diameter of 3-5 mm, and the pills were freeze-dried. A total of 10,000 g was made and packed in 4.8 g units.

Since the constituent components of the present invention are widely known as safe food materials and are registered as safe food ingredients in Korea Food and Drug Administration, they can be directly applied to human body (clinical) without in vitro experiment, animal experiment or biomarker test, Experiments were carried out and the effectiveness of the study was confirmed by interviewing or observing the patients.

Clinical Trials

Clinical Trial 1—Improvement of Edema (43 Years Old, Female)

After receiving thyroid cancer surgery, she was a long-term female patient taking Synthroid, a thyroid drug. Due to the toxicity of the medicine, the whole body swelled every morning, and the face and the fingers especially continued to swell a lot. As the food composition of the present invention was started to eat by one unit twice a day (b.i.d.), the swelling of the face disappeared within 7 days and the swelling of the whole body could not be observed visually in 5 days. We could confirm that weight was reduced by 2.0 kg. The patient stated that she was lighter on her own, her face was smaller, and her skin was better. Treatment of edema usually does not have a satisfactory effect, although limiting salt intake or administering a diuretic. According to the present invention, it was confirmed that the edema improvement effect was very rapid. Edema is caused by congestion of body fluids, and congestion of body fluids is caused by lymphatic circulation disorders, so improved edema means improved lymphatic circulation.

Clinical Trial 2—Improvement of Edema (Age 54, Female)

This patient was a 54-year-old pharmacist who frequently developed allergies and swelling. She had degenerative arthritis and her knees were swollen all the time. She was bitten by a mosquito a few days ago, but she left it, and after two days her arms and throat were swollen a lot. She applied steroid ointment, but was more swollen and feverish. Two units of the food composition according to the present invention were simultaneously administered, and then the two units were simultaneously administered 5 hours later. The next morning, swelling of the arms and neck was scarcely observed. After that, she was allowed to take one unit of the food composition according to the present invention twice a day (b.i.d.) for 5 days, and no swelling of the knee was observed any more. Edema is caused by congestion of body fluids, and congestion of body fluids is caused by lymphatic circulation disorders, so improved edema means improved lymphatic circulation.

Clinical Trial 3—Improvement of Edema (40 Years Old, Female)

She was a plump and fleshy female patient, with frequent swelling of the instep and soles, and with sore throat and sore shoulder. Two units of the food composition according to the present invention were administered three times a day (t.i.d.) for five days. Five days after taking it, she stated that instep and soles swelling completely disappeared. It was judged that waste of whole body was exhausted by promoting lymphatic circulation.

Clinical Trial 4—Improvement of Edema (72 Years, Female)

She was a female patient with a skin patch that had edema for more than 10 years. The skin was sensitive, and she felt pain in my hand. She has taken the Entelon Tab (150 mg), which is marketed as a circulatory drug, for years, but it has not improved. This patient was administered with the food composition according to the present invention by 3 units three times a day (t.i.d.) for 20 days. After 20 days, it was visually confirmed that edema was reduced to such an extent that the skin of the calf was wrinkled. Edema is caused by congestion of body fluids, and congestion of body fluids is caused by lymphatic circulation disorders, so improved edema means improved lymphatic circulation.

The following clinical test results are, of course, physiologically predictable results when the lymphatic circulation is promoted.

Clinical Trial 5—Pain Improvement (48 Years Old, Female)

She was a pharmacist and complained that her wrist pain was so severe that she could not get a 500 g medicine box from the pharmacy. The food composition according to the present invention was administered by two units three times a day (t.i.d) for one day. She stated that wrist pain was relieved from the first dose, and she stated that wrist pain had disappeared completely on the 3rd day.

Clinical Trial 6—Pain Improvement (50 Years Old, Female)

She was a patient who had been in the market for more than 30 years. She was suffering from ankle pain and heel pain and had been taking acupuncture and analgesics for a long time. The food composition according to the present invention was administered in two units by three times a day (t.i.d.) for 2 days, followed by a single unit twice a day (b.i.d.) for 10 days. After about two weeks he stated that he no longer felt ankle and heel pain.

Clinical Trial 7—Pain Improvement (80 Years Old, Female)

She was an old patient who had a back surgery and a knee artificial operation, and all the body was carrying a sore cane. The food composition according to the present invention was administered by two units three times a day (t.i.d.) for 10 days, and after 10 days, followed by one unit twice a day (b.i.d.) for 3 months. The patient stated that the pain in his back and knee had been alleviated from about 2 days later, and all the pain had disappeared after 70 days.

Clinical Trial 8—Pain Improvement (61 Years Old, Female)

She was a nursing care worker from China. She had a backache from her youth. She seemed to have a lot of back pain and thigh pain. Taking the food composition according to the present invention by two units three times a day (t.i.d.) for 10 days, the patient stated that the pain was alleviated after 10 days. After 10 days, she took by one unit twice a day (b.i.d.) for 3 months. She stated that not only back pain but also thigh pain had disappeared after 3 months.

Clinical Trial 9—Pain Improvement (31 Years Old, Female)

This patient was a 31 year old female athlete. This patient injured the Achilles tendon during training. The patient received hospital treatment for a considerable period of time, but no improvement in symptoms at all. This patient was not only unable to jump, but also difficult to walk. The Achilles tendon was swollen with inflammation and severe edema. When the food composition according to the present invention was administered by 3 units three times a day (t.i.d.) for 3 days, the Achilles tendon was not painful for touching and massage, and the pain was improved to such an extent that it would not hinder walking. Thereafter, the food composition according to the present invention was allowed to take by two units three times a day (t.i.d.) for 7 days, and it became possible to jog with morning exercise. After the administration of the food composition according to the present invention for 7 days, the exercise intensity was increased by 90%, and the Achilles tendon was hardly painful. The strong lymphatic circulation promoted the Achilles tendon to restore injury.

Clinical Trial 10—Inflammation Improvement (42 Year Old Male)

This patient had been riding a motorcycle before, and the Achilles tendon was broken by accident. Since then, inflammation has worsened almost every year and dozens of re-operations and treatments have been done, but the inflammation has not been cleaned. At the Seoul National University Hospital in Korea, doctors confirmed the infection of super bacteria and virus at the wound site and said that it could no longer be cured by surgery or pharmacotherapy. In addition, if the inflammation worsens, it is recommended to cut the ankle because of the risk of systemic infection. In this state, when the food composition according to the present invention was intensively administered by 4 units three times a day (t.i.d) for five days, the inflammation was largely reduced after dark black blood came out from the inflammation site. Thereafter, when the food composition according to the present invention was administered by 3 units three times a day (t.i.d.) for 7 days, the inflammation subsided cleanly and there was no inconvenience caused by the affected part. Naturally, there was no ankle amputation, and the super bacteria or virus was no longer identified when re-examined at the hospital. In this case, it was thought that the food composition according to the present invention strengthened the immune function and helped immune cell movement, thereby removing super bacteria and viruses in the inflammation site, and the inflammation disappeared.

Clinical Trial 11—Promotion of Cell Regeneration by Improvement of Cell Environment (Male, 45 Years Old)

The patient injured his hand dermis due to the accident involving the hand on the belt. It was diagnosed that it was impossible to regenerate the skin because the wound was over 5 centimeters wide. When the food composition according to the present invention was administered by 3 units three times a day (t.i.d.) for 9 months, most of the skin was regenerated and it was visually confirmed that the keloid was also very small compared to the area of the damaged area. Reducing an already existing keloid to improve scarring is a lengthy, time-consuming and difficult task. By utilizing the food composition according to the present invention, the body fluid circulation can be actively promoted to rapidly release inflammatory substances or toxic substances from damaged skin to prevent inflammation, to improve pain, to help immune cell migration. It improves the inflammation caused by microbial infection, and smoothes the supply of nutrients, oxygen and water necessary for skin regeneration, thereby helping skin regeneration.

Clinical Trial 12—Promotion of Cell Regeneration by Improvement of Cell Environment (29 Years Old, Female)

This patient was a mother who delivered through a cesarean section in the late 20s. From 4 weeks after birth, the food composition according to the present invention was administered by 2 units twice a day (b.i.d.) for 12 months. At first, the hard part of the cesarean section changed smoothly, and after 8 months, it was confirmed that no keloid was formed. Cesarean section surgery involves the incision and re-stitching to the skin and subcutaneous tissue of the thick abdomen. Therefore, the wound at the surgical site is exceptionally deep. Therefore, scar on the incision surface is seen on the surface after the operation, and a keloid mass such as a thick stick of ball pen is touched in the scar. In the case of cesarean section with severe damage to the subcutaneous tissue, keloid is not produced, and it seems possible to reduce scar by preventing keloid formation of other operation or wound.

Clinical Trial 13—Promotion of Cell Regeneration by Improvement of Cell Environment (35 Years Old, Male)

This patient was a burned male patient. The patient had been burned more than one year ago and the keloid formation was already complete, making it impossible to reduce the scar. Skin transplantation showed a thick layer of skin at the scar site. When the food composition according to the present invention was administered by 3 units three times a day (t.i.d.) for 8 months, resulting in thinning of the skin layer and reduced scarring as the keloid decreased. The principle of scar removal is not to eliminate the keloid directly but to promote the lymphatic circulation and improve the environment of the damaged dermis tissue to help normal skin cells develop. Then the keloid is no longer produced, and the keloid that has already formed is peeled away gradually over time. The scar management that has already occurred is time consuming to be recovered from the dermis layer, and burn scar management is especially difficult because of the formation of keloid. The improvement of these burn scars gives new hope not only to burn scars but also to general scar improvement.

Clinical Trial 14—Bruising (48 Years Old, Female)

During the cosmetic imbedding procedure under the eyes, the patient had blood vessels under her eyes bursting, and there was a wide spread of dark red contusion under the eyes. In the case of this patient, the hospital diagnosed that it took 3-6 months for the contusion to be removed due to severe bruising. After taking the food composition of the present invention by 2 units three times a day (t.i.d.) for 7 days, the bruises were removed to the extent that it was hardly observed with the naked eye. According to the lymphatic circulation principle, when the lymphatic circulation is promoted, the bruising easily disappears.

Clinical Trial 15—Elimination of Bruises (32 Years Old, Female)

She was a female patient with bruises caused by the attack around the eyes. The food composition according to the present invention was administered by 2 units three times a day (t.i.d.) for 5 days. It was visually observed that all of the bruises had disappeared with only small traces of staining after 5 days.

Clinical Trial 16—Body Temperature Control (50 Years Old, Female)

This patient was a middle-aged woman with a climacteric symptom who feels very tired without any reason, had a cold buttock and a stomach, felt warm on his back, and felt cold all over the body in the morning. The food composition according to the present invention was administered by two units twice a day (b.i.d.) for one month. After one month, the hips and the stomach felt less cold, the warmth of their backs disappeared. And she no longer felt cold in the morning. Above all, he stated that she no longer felt fatigue and was able to find vitality in his body.

Clinical Trial 17—Promoting Drug Delivery (45, Female)

This patient was a patient with chronic cystitis. This patient had taken Septrine Tab (antibiotic for cystitis treatment) when the cystitis was severe. However, there were frequent cases where the effect was not seen even after taking the Septrin Tab. This patient was given a food composition according to the present invention along with Septrin Tab. The patient then stated that the effect of taking the Septin Tab was rapid and that the symptoms improved more clearly than before. According to the present invention, the efficacy of Septrin Tab was rapidly and reliably transferred to the bladder by the food composition and it was judged that Septrin Tab was effectively acting on the affected bladder.

Clinical Trial 18-Promoting Drug Delivery (68 Years, Male)

There was a relatively wide spread of herpes zoster around the mouth. Aciclovir ointment(antibiotic ointment for herpes zoster treatment) was prescribed in the hospital and applied for a week, but there was no improvement. Again, the patient was prescribed a Famclean tab (antibiotic tab for herpes zoster treatment) for a week, but the symptoms did not improve much. The food composition according to the present invention was administered by 2 units to Famclean Tabs at the same time. Within two days, the herpes zoster disappeared and only the traces remained visually.

Manufacturing and Sales

The food composition products according to the present invention were manufactured in the following composition ratios and packing units.

First, a mixture of 27% by weight of cnidium powder, 14% by weight of dried bigarade orange powder, 11% by weight of kalopanax powder and 8% by weight of coix powder was prepared, and 26% by weight of maple syrup and 14% by weight of bambusae succus were further mixed. The mixture was molded into small pills having a diameter of 3.8 mm, lyophilized, and packed in a stick pack of 4.8 g.

Figure 2:
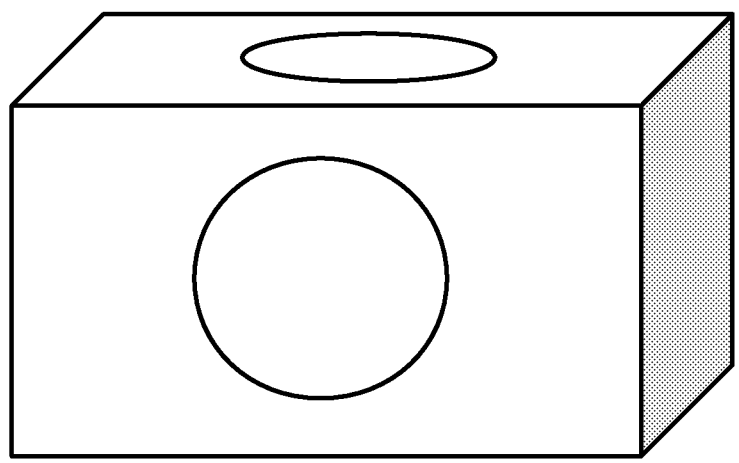
FIG. 2 is a photograph of the product package of the food composition according to the present invention.

FIG. 1 is a photograph of the product contents of the food composition according to the present invention, and FIG. 2 is a photograph of the product packaging of the food composition according to the present invention.

The inventor sold more than 6,000,000 stick packs (4.8 grams per stick pack) at 2,000 pharmacies in Korea from May 1, 2017 to Mar. 31, 2018. The pharmacists who participated in the sale tracked the results of administration to 2,000 patients with edema, and found that 1,960 (98%) patients had a reduction in edema and a weight loss of 1.0% to 5.0%.

What is claimed is:

1. A food product for improving lymphatic circulation, comprising:
    a packet;
    contained in the packet, multiple freeze-dried pills that each have a diameter of 3-5 mm, each pill comprising a mixture of:
    about 27% by weight of cnidium powder;
    about 26% by weight of maple syrup;
    about 14% by weight of dried bigarade orange powder;
    about 14% by weight of bambusae succus that is a collection of sap of bamboo that is evaporated by high heat in the process of making charcoal with bamboo;
    about 11% by weight of kalopanax powder; and
    about 8% by weight of coix powder;
    and thereby the mixture shows the effect of a reduction in edema by improving lymphatic circulation.

2. The food product for improving lymphatic circulation of claim 1, wherein the total weight of the multiple freeze-dried pills in the packet is about 4.8 grams.

* * * * *